United States Patent [19]
Wen et al.

[11] Patent Number: 6,066,675
[45] Date of Patent: May 23, 2000

[54] METHOD FOR TREATMENT OF RETINAL DISEASES

[75] Inventors: Rong Wen, Bala Cynwyd, Pa.; Roy H. Steinberg, deceased, late of San Francisco, Calif., by Jane M. Gitschier, executor; Matthew M. Lavail, San Francisco, Calif.

[73] Assignee: The Regents of the University of California, Oakland, Calif.

[21] Appl. No.: 08/925,544

[22] Filed: Sep. 8, 1997

Related U.S. Application Data

[60] Provisional application No. 60/025,232, Sep. 13, 1996.

[51] Int. Cl.$^7$ .................................................. A61K 31/135
[52] U.S. Cl. .......................... 514/649; 514/652; 514/912
[58] Field of Search .................................. 514/649, 652, 514/912

[56] References Cited

U.S. PATENT DOCUMENTS

| | | |
|---|---|---|
| 3,906,949 | 9/1975 | Holland . |
| 4,007,268 | 2/1977 | Voorhees . |
| 4,235,871 | 11/1980 | Papahadjopoulos et al. . |
| 4,501,728 | 2/1985 | Geho et al. . |
| 4,837,028 | 6/1989 | Allen . |
| 5,019,369 | 5/1991 | Presant et al. . |
| 5,667,968 | 9/1997 | Lavail . |

OTHER PUBLICATIONS

Faktorovich et al., Nature, 347:83–86, Sep. 6, 1990.
Wen et al., J. Neurosci., 15:11:7377–7385, Nov. 1995.
Baird, A., "Fibroblast growth factors: activities and significance of non–neurotrophin neurotrophic growth factors, "Curr. Opin, Neurobiol. 4:78–86 1994).
Bittiger, H. et al., "Are only $\alpha_2$–adrenergic receptors present in bovine retina?,"Nature 287:645–647 (1980).
Bowman, L.H. et al., "Multiphe ribosomal RNA cleavage pathways in mammalian cells," Nucl. Acids Res. 9(19) : 4951–4966 (1981).
Burney, I.A. et al., "Effect of Vasoactive Drugs on Tumor Blood Flow as Determined by $^2$H Nuclear Magnetic Resonance Spectroscopy,"Acta Oncologica 34(3) :367–371 (1995).
Bush, R.A. et al., "The Effect of Unilateral Optic Nerve Section on Retinal Light Damage in Rats," Exp. Eye Res. 52 : 139–153 (1991).
Bylund, D.B., "Subtypes of $\alpha_1$–and $\alpha_2$–adrenergic receptors," FASEB J. 6:832–839 (1992).
Elena, P–P. et al., "Autoradiographic Localization of Beta–Adrenergic Receptors in Rabbit Eye," Invest. Opthalmology and Vis. Sci. 28 (8) : 1436–1441 (1987).
Elena, P–P et al., "Beta Adrenergic Binding Sites in the Human Eye: An Autoradiographic Study, " J. Ocu. Pharm. 6 (2) :143–149 (1990).
Ferrari–Dileo, G., "Beta$_1$ Beta$_2$ Adrenergic Binding Sites in Bovine Retina and Retinal Blood Vessels," Invest. Opthalmology and Vis. Sci. 29 (5) :695–699 (1988).

Follesa, P. et al., "Regulation of Basic Fibroblast Growth Factor and Nerve Growth Factor mRNA by β–Adrenergic Receptor Activation anf Adrenal Steroids in Rat Central Nervous System," Mol. Pharm. 43:132–138 (1993).
Gao, H. etal., "Basic Fibroblast Growth Factor in Retinal Development: Differential Levels of bFGF Expression and Content in Normal and Retinal Degeneration (rd) Mutant Mice,"Devel. Biol. 169:168–184 (1995).
Gao, H. et al., "Basic Fibroblast Growth Factor: Increased Gene Expression in Inherited and Light–Induced Photoreceptor Degeneration," Exp. Eye Res. 62:181–189 (1996).
Jakobs, K.H., "Inhibition of adenylate cyclase by hormones and neurotransmitters," Mol. Cell. Endocrin.16:147–156 (1979).
Kostyk, S.K,. et al., "Optic Nerve Injury Alters Basic Fibroblast Growth Factor Localization in the Retina and Optic Tract," J. Neurosci. 14 (3):1441–1229 (1994).
LaVail, M.M. et al., "Influence of Eye Pigmentation and Light Deprivation on Inherited Retinal Dystrophy in the Rat," Exp. Eye Res. 21:167–192 (1975).
Osborne, N.N., "Binding of (—) [$^3$H] Noradrenaline to Bovine Membrane of the Retina. Evidence for the Existence of $\alpha_2$–Receptors," Vision Res. 22:1401–1407 (1982).
Osborne, N.N., "Inhibition of cAMP prodution by $\alpha_2$–adrenoceptor stimulation in rabbit retina," Brain Res. 553:84–88 (1991).
Park, C.M. et al., "Growth Factor–Induced Retinal Regeneration in Vivo, " Int'Rev. Cytol. 146:49–74 (1993).
Shimasaki, S. et al., "Complementary DNA cloning and sequencing of rat ovarian basic fibroblast growth factor and tissue distribution study of its mRNA," Biochem. Biophys. Res. Commun. 157(1) :256–263 (1988).
Stachowiak, M.K. et al., "Regulation of bFGF Gene Expression and Subcellular Distribution of bFGF Protein in Adrenal Medullary Cells," J. Cell Biol. 127(1) ;203–223 (1994).
Steinberg, R.H., "Survival factors in retinal degenerations, "Curr. Opin. Neuro. 4:515–5224 (1994).
Szoka, F. et al., "Comparative properties and methods of preparation of lipid vesicles (lipsomes) ,"Ann. Rev. Biophys. Bioeng. 9:467–508 (1980).
Wagner, J.A. "The Fibroblast Growth Factors: An Emerging Family of Neural Growth Factors," Curr. Topics Microbiol. Immunol. 165:95–118 (1991).
Wen, R. et al., "Injury–Induced Upregulation of bFGF and CNTF mRNAS in the Rat Retina,"J. Neurosci. 15 (11) : 7377–7385 (1995).
Wikberg–Matsson, A. et al., "Characterization of $\alpha_{2A}$–Adrenoceptor Subtypes in the Procine Eye: Identification of $\alpha_{2c}$ –Adrenoceptors in the Retina," Exp. Eye Res. 63:57–66 (1996).
Zarbin, M.A. et al., "Autoradiographic Localization of High Affinity GABA, Benzodiazepine, Dopaminergic, Adrenergic and Muscarinic Cholinergic Receptors in the Rat, Monkey and Human Retina," Brain Res. 374:75–92 (1986).

Primary Examiner—Zohreh Fay
Attorney, Agent, or Firm—Cooley Godward LLP

[57] ABSTRACT

Methods for the stimulation of growth factor expression and for treatment of retinal diseases with alpha- and beta-adrenergic agonists are disclosed.

16 Claims, 4 Drawing Sheets

METHOD FOR TREATMENT OF RETINAL DISEASES

This application claims the benefit of the priority date of U.S. Provisional Application No. 60/025,232, filed Sep. 13, 1996, the disclosure of which is incorporated by reference in entirety for all purposes.

ACKNOWLEDGEMENTS

This invention was supported in part by grants from the National Institutes of Health (EY01429, EY01919 and EY06842). The U.S. government may have rights in this invention.

BACKGROUND OF THE INVENTION

In human retinal diseases, blindness is often caused by injury and death of photoreceptors and ganglion cells, such as in inherited retinal degenerations and in age-related macular generation, glaucoma, and optic nerve injury.

Basic fibroblast growth factor (bFGF) when injected into the eye can rescue photoreceptors in Royal College of Surgeon (RCS) rats which have an inherited retinal degeneration, and in rats that have been light damaged by exposure to constant light (see, for example, Steinberg, *Curr. Opin. Neurobiology* 4:515–524 (1994)).

Basic fibroblast growth factor (bFGF) is one of the best characterized members of a family of at least nine structurally related heparin binding growth factors (Baird *Curr. Opin. Neurobiology* 4:78–86 (1994)). bFGF exhibits neurotrophic activities (Wagner, J. A. *Curr. Top. Microbiol. Immunol.* 165:95–118 (1991); Baird *Curr. Opin. Neurobiol.* 4:78–86 (1994)), including retinal regeneration in vivo (Park et al. *Int. Rev. Cytol.* 146:49–74 (1993)).

In the brain, bFGF expression is elevated by various insults, including mechanical trauma, chemical injury, and ischemia (Wagner, J. A. *Curr. Top. Microbiol. Immunol.* 165:95–118 (1991); Baird *Curr. Opin. Neurobiol.* 4:78–86 (1994)). In addition, activation of β-adrenergic receptors increased bFGF mRNA in rat hippocampus, cerebral cortex, and cerebellum (Follesa et al. *Mol. Pharmacol.* 43:132–138 (1993)). Recently, it has been shown in rat retina that bFGF mRNA was up-regulated by mechanical injury (Wen et al. *J. Neurosci.* 15:7377–7385 (1995)).

Increased bFGF immunoreactivity in the photoreceptors has been reported in both mouse and rat after optic nerve crush (Kostyk et al. *J. Neurosci.* 14:1441–1449 (1994)), whereas expression of bFGF mRNA was found to be elevated in mouse and rat after constant light exposure (Gao et al. *Exp. Eye. Res.* 62:181–189 (1996)). In addition, mechanical injury to the mouse or rat retina induced a marked increase in bFGF expression, and the greatest increase was found in the inner nuclear layer (Wen et al. *J. Neurosci.* 15:7377–7385 (1995)).

The neuroprotective activities of bFGF have been well studied (Wagner, J. A. *Curr. Top. Microbiol. Immunol.* 165:95–118 (1991); Baird *Curr. Opin. Neurobiol.* 4:78–86 (1994)) and evidence is accumulating that bFGF promotes photoreceptor survival. Optic nerve crush upregulates bFGF expression in photoreceptors (Kostyk et al. *J. Neurosci.* 14:1441–1449 (1994)), which is believed to result in photoreceptor protection against light damage in rats after optic nerve section (Bush et al. *Exp. Eye Res.* 52:139–153 (1994)). Gao and Hollyfield (*Dev. Biol.* 169:168–184 (1995); *Exp. Eye Res.* 62:181–189 (1996)) found that bFGF in photoreceptors was elevated in light-stressed mice and rats, and also in inherited mouse retinal degeneration models. They suggest that bFGF upregulation may function to enhance photoreceptor survival. In addition, upregulation of bFGF in retina by mechanical injury is believed to be responsible for the injury-induced photoreceptor rescue in RCS and light-damaged rats (Wen et al. *J. Neurosci.* 15:7377–7385 (1995)).

Also relevant to the instant invention are alpha- and beta-adrenergic receptors in the eye. Alpha-2-adrenergic receptors have been identified in the retina. Binding studies with bovine retinal membranes showed that the major α-adrenergic receptor in the retina was of the $\alpha_2$ subtype (Bittiger et al. *Nature* 287:645–647 (1980); Osborne *Vis. Res.* 22:1401–1407 (1982)). Using [$H^3$]para-aminoclonidine and autoradiography, Zarbin et al. (*Brain Res.* 374:75–92) mapped $\alpha_2$-adrenergic receptors in the rat retina. Recently, subtypes of alpha-2-adrenergic receptors have been characterized in the pig eye, and both the alpha-2A- and alpha-2C- subtypes are found in the retina (Wikberg-Matsson et al. *Exp. Eye Res.* 63:57–66 (1996)). Beta-adrenergic binding sites ($beta_1$ and $beta_2$ types) have been localized and characterized in the human eye (Elena et al. *J. Ocular. Pharmacology* (Summer, 6(2):143–9 (1990)); Elena, et al. *Investigative Opth.* 28:1436–1441 (1987)); Ferrari-Dileo *Investigative Opth.* 28:695–699 (1988)). The roles of the α- and β-adrenergic receptors in the eye are not understood at this time.

A need exists for methods and compounds for use in the treatment of diseases of the retina. The instant invention addresses this need and others.

SUMMARY OF THE INVENTION

One aspect of the invention is a method for stimulating expression of a growth factor in a patient comprising administering to the patient an effective dose of an alpha-adrenergic agonist. The growth factor can be basic fibroblast growth factor (bFGF). The agonist can be administered systemically or locally. The growth factor expression, including bFGF expression, can be stimulated in retinal cells in the patient, especially photoreceptors. The photoreceptors may be injured or dying.

Another aspect of the invention is a method for treating retinal disease, comprising administering to a patient a therapeutically effective dose of alpha-adrenergic agonist. The agonist can be administered systemically or to the eye. In some embodiments, bFGF expression is stimulated in retinal cells in the patient, especially in photoreceptors. The photoreceptors may be injured or dying.

A further aspect of the invention is a method for stimulating expression of a growth factor in a patient comprising administering to the patient an effective dose of a beta-adrenergic agonist. The growth factor can be basic fibroblast growth factor (bFGF). The agonist can be administered systemically or locally. The growth factor expression, including bFGF expression, can be stimulated in retinal cells in the patient, especially photoreceptors. The photoreceptors may be injured or dying.

Another aspect of the invention is a method for treating retinal disease, comprising administering to a patient a therapeutically effective dose of a beta-adrenergic agonist. The agonist can be administered systemically or to the eye. In some embodiments, bFGF expression is stimulated in retinal cells in the patient, especially in photoreceptors. The photoreceptors may be injured or dying.

DESCRIPTION OF THE SPECIFIC EMBODIMENT

Figure 1A:
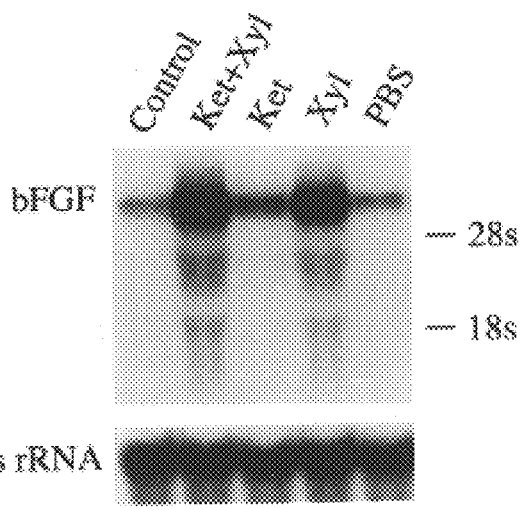
FIGS. 1(A–C) depicts (A) xylazine-induced bFGF expression; (B) time course of xylazine-induced bFGF expression; and (C) inhibition of xylazine effect by yohimbine.

The term "agonist" as used herein is intended to refer to agents which directly or indirectly combine with receptors on an effector cell and initiate or stimulate a response in the effector cell. A directly acting agonist produces a response in effector cells by directly interfacing with receptors on those cells. An indirectly acting agonist does not interact directly with receptors on effector cells, but is capable of producing sympathetic effects (see, for example, Hoffman and Lefkowitz, "Catecholamines and Syspathominetic Drugs", in *The Pharmacological Basis of Therapeutics*, Ralli et al., eds., 8th eds. Pergamon Press, N.Y.). The alpha- and beta-adrenergic agonists of the invention include but are not limited to such compounds as norepinephrine, clonidine, guanfacine, azepexole, B-HT 920, UK-14,304, epinephrine, dipivefrin, apraclonidine, brimonidine, agmatine, p-aminoclonidine, guanabenz, p-iodoclonidine, oxymetazoline, xylazine, salbutamol, dobutamine, isoproterenol, nylidrin, and clenbuterol (see, for example, *Clinical Ocular Pharmacology*, Bartlett, J. D., and Jaanus, S. D., eds. Butterworth-Heinemann, Boston (1995)). Also included in this definition are antibodies which bind to alpha- or beta-adrenergic receptors, including but not limited to polyclonal antibodies, monoclonal antibodies, single chain antibodies, $F_{ab}$, $F_{ab}'$, $F_v$, and antibody fragments. Small molecules which can bind to alpha- or beta-adrenergic receptors and stimulate a response in cells bearing such receptors are also included in the scope of this definition. Such small molecules can be generated by combinatorial chemistry, phage display, and other techniques well known in the art. Preferably, the alpha- and beta-agonists of the invention are capable of passing the blood-retinal barrier.

One embodiment of the invention is the upregulation of growth factors by alpha- and beta-adrenergic agonists. In a preferred embodiment, bFGF expression is stimulated by an alpha-adrenergic agonist.

In an embodiment of the invention, alpha- and/or beta-adrenergic agonists can be utilized to treat any condition which results in injury or death of photoreceptors or other retinal cells, including retinal detachment, age-related and other maculopathies, photic retinopathies, surgery-induced retinopathies (either mechanically or light-induced); toxic retinopathies; retinopathy of prematurity; viral retinopathies such as CMV or HIV retinopathy elated to AIDS; uveitis; ischemic retinopathies due to venous or arterial occlusion or other vascular disorders; retinopathies due to trauma or penetrating lesions of the eye; peripheral vitroretinopathy, and inherited retinal degenerations such as, but not limited to, the various forms of retinitis pigmentosa. In an embodiment of the invention, retinal disease is treated by administration of an alpha-adrenergic agonist. Preferably, the retinal disease is characterized by injury or death of photoreceptors. In a further embodiment, retinal disease is treated by administration of a beta-adrenergic agonist. In yet a further embodiment, the alpha- and beta-agonists can be used in combination.

Alpha- and/or beta-adrenergic receptor agonists can be delivered to the eye through a variety of routes, including but not limited to intraocularly, by topical application to the eye or by intraocular injection into, for example, the vitreous or subretinal (interphotoreceptor space); locally by insertion or injection into the tissue surrounding the eye; systemically through an oral route or by subcutaneous, intravenous or intramuscular injection; or via catheter or implant. The agonists invention can be administered prior to the onset of the condition, to prevent its occurrence, such as during eye surgery, immediately after the onset of the pathological condition, or during the occurrence of an acute or protracted condition.

In therapeutic applications, agonist compositions are administered to a patient in an amount sufficient to lessen, ameliorate, to cure or at least partially arrest symptoms and/or complications. This amount is defined as a "therapeutically effective dose." Amounts effective for this use will depend on, e.g., the agonist composition, the manner of administration, the stage and severity of the disease being treated, the weight and general state of health of the patient, and the judgment of the prescribing physician. In some embodiments of the invention, an "effective dose" of an alpha- or beta-adrenergic agonist is a dose sufficient to stimulate growth factor mRNA transcription.

For therapeutic use, administration is preferably begun at the first sign of retinal injury or disease or shortly after diagnosis in the case of acute injury, although the treatment is appropriate throughout the course of retinal disease. This is followed by maintenance doses until at least symptoms are substantially abated and preferably for a period thereafter. Maintenance doses may be daily, more preferably weekly, most preferably monthly. In chronic conditions and with acute injuries, loading doses followed by maintenance doses may be required. Where slow-release, encapsulated, or depot-type deliveries are used, maintenance doses are preferably administered weekly, biweekly, monthly, or at other periodic intervals.

Treatment of an affected individual with the compositions of the invention may hasten resolution of the disease in acutely affected individuals. For those individuals susceptible (or predisposed) to developing chronic disease the compositions are useful in methods for preventing the evolution from acute to chronic disease on the onset. Where the susceptible individuals are identified prior to onset the composition can be targeted to them, minimizing need for administration to a larger population.

The pharmaceutical compositions for therapeutic treatment are intended for parenteral, topical, oral or local administration. Preferably, the pharmaceutical compositions are administered parenterally, e.g., intravenously, subcutaneously, intradermally, or intramuscularly. Thus, the invention provides compositions for parenteral administration which comprise a solution of the agonist dissolved or suspended in an acceptable carrier, preferably an aqueous carrier. A variety of aqueous carriers may be used, e.g., water, buffered water, 0.8% saline, 0.3% glycine, hyaluronic acid and the like. These compositions may be sterilized by conventional, well known sterilization techniques, or may be sterile filtered. The resulting aqueous solutions may be packaged for use as is, or lyophilized, the lyophilized preparation being combined with a sterile solution prior to administration. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc.

The concentration of agonists in the pharmaceutical formulations can vary widely, i.e., from less than about 0.1%, usually at or at least about 2% to as much as 20% to 50% or more by weight, and will be selected primarily by fluid volumes, viscosities, etc., in accordance with the particular mode of administration selected.

The agonists of the invention may also be administered via liposomes. Liposomes include emulsions, foams, micelles, insoluble monolayers, liquid crystals, phospholipid dispersions, lamellar layers and the like. In these preparations the agonist to be delivered is incorporated as part of a liposome, alone or in conjunction with a molecule which binds to a desired target, such as a photoreceptor, or with other therapeutic or immunogenic compositions. Thus, liposomes either filled or decorated with a desired agonist of the invention can delivered systemically, or can be directed to the eye, where the liposomes then deliver the selected therapeutic/immunogenic peptide compositions. Liposomes for use in the invention are typically formed from standard vesicle-forming lipids, which generally include neutral and negatively charged phospholipids and a sterol, such as cholesterol. The selection of lipids is generally guided by consideration of, e.g., liposome size, acid lability and stability of the liposomes in the blood stream. A variety of methods are available for preparing liposomes, as described in, e.g., Szoka et al. *Ann. Rev. Biophys. Bioeng.* 9:467 (1980), U.S. Pat. Nos. 4,235,871, 4,501,728, 4,837,028, and 5,019,369, incorporated herein by reference.

A liposome suspension containing an agonist may be administered intravenously, locally, topically, etc. in a dose which varies according to, inter alia, the manner of administration, the agonist being delivered, and the stage of the disease being treated.

For solid compositions, conventional nontoxic solid carriers may be used which include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 10–95% of active ingredient, that is, one or more agonists of the invention, and more preferably at a concentration of 25%–75%.

For aerosol administration, the agonists are preferably supplied in finely divided form along with a surfactant and propellant. Typical percentages of agonists are 0.01%–20% by weight, preferably 1%–10%. The surfactant must, of course, be nontoxic, and preferably soluble in the propellant. Representative of such agents are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides may be employed. The surfactant may constitute 0.1%–20% by weight of the composition, preferably 0.25–5%. The balance of the composition is ordinarily propellant. A carrier can also be included, as desired, as with, e.g., lecithin for intranasal delivery.

The alpha- and beta-agonists of the invention can additionally be delivered in a depot-type system, an encapsulated form, or an implant by techniques well-known in the art. Similarly, the agonist can be delivered via a pump to the eye or other tissue.

In some embodiments, the alpha- and beta-agonists can be used in combination with other therapies to treat retinal disease.

The following examples are offered by way of illustration, not limitation.

Experimental Examples

In the following experiments, an unexpected induction of basic fibroblast growth factor (bFGF) mRNA in the rat retina was observed after systemic administration of the $\alpha_2$-adrenergic agonists xylazine and clonidine. A single injection of xylazine or clonidine transiently increased bFGF mRNA. Preinjection of yohimbine, an $\alpha_2$-adrenergic antagonist, completely inhibited this increase. Higher dosage of yohimbine inhibited the baseline expression of bFGF. The induced bFGF expression occurred almost exclusively in the inner segment region of photoreceptors. No increase in bFGF mRNA was found in the brain after either xylazine or clonidine injection. Xylazine or clonidine given systemically before and during constant light exposure also reduces photoreceptor degeneration in albino rats. These results indicate that endogenous bFGF promotes photoreceptor survival.

A. Materials and Methods

1. Animals

Male Sprague-Dawley rats, 2–3 months of age, were used in all experiments. Animals were kept in a 12:12-hour light-dark cycle at an in-cage illuminance of <25 foot-candles (1 ft-c=10.76 lux) for 7 d days before experiments. Ketamine (Fort Dodge Laboratories Inc., Fort Dodge, IW), xylazine (either from Lloyd Laboratories, Shenandoah, IW, or Sigma, St. Louis, Mo.), or phosphate-buffered saline (PBS) was injected intramuscularly into the right hind leg. Clonidine (Sigma) or yohimbine (Sigma) was injected intraperitoneally.

2. Northern blot analysis

Animals were killed by carbon dioxide ($CO_2$) overdose. Whole retinas were dissected, snap frozen in liquid nitrogen, and stored at −80° C. Pooled retinas were homogenized in 5.5 M guanidinium thiocyanate solution (5.5 M guanidinium thiocyanate, 25 mM sodium citrate, and 0.5% sodium lauryl sarcosine, pH 7.0) and total RNA was isolated by a CsTFA (cesium trifluoroacetate, Pharmacia, Piscataway, N.J.) gradient method (Farrell (1993) *RNA methodologies: A laboratory guide for isolation and characterization*. pp 64–67. San Diego: Academic Press). Total RNA (20 µg of each sample) was electrophoresed on 1% agarose formaldehyde gels and downward wick transferred in 20×SSC (1×SSC= 0.15 M NaCl and 0.15 M sodium citrate, pH 7.0) to a nylon membrane (Hybond-N, Amersham, Arlington Heights, Ill.). Blots were UV irradiated to immobilize RNA and then prehybridized for 4 hr in a hybridization solution containing 50% formamide, 5× Denhardt's solution, 5×SSPE (1×SSPE=0.15 M NaCl, 10 mM $NaH_2PO_4$, 1 mM EDTA, pH 7.4), 200 µg/ml denatured salmon sperm DNA, and 5% SDS at 50° C. Random primed $^{32}P$ labeled cDNA probes for rat bFGF (gift of Dr. A. D. Baird, Whittier Institute for Diabetes and Endocrinology, La Jolla, Calif.; Shimasaki et al. *Biochem. Biophys. Commun.* 157:256–263 (1988)), or rat 18s rRNA (gift of Dr. D. Schlessinger, Washington University, St. Louis, Mo.; Bowman et al. *Nucl. Aci. Res.* 9:4951–4966) were added to the hybridization buffer ($10^6$ cpm/ml) and hybridized at 50° C. overnight. Blots were then washed twice in 2×SSC, 0.1% SDS at room temperature for 5 min and twice in 0.1×SSC, 0.1% SDS at 65° C. for 10 min. After posthybridization wash, blots were exposed to a Storage Phosphor Screen (Molecular Dynamics, Sunnyvale, Calif.) and data were digitized by scanning the phosphor screen with a Phosphor Imager System (Molecular Dynamics). Blots were reprobed then with 18s rRNA probe, and data of 18s rRNA served as a control for RNA loading. Quantitative analysis was performed for the 7.0 kb transcript of bFGF mRNA, normalized with data of 18s rRNA, using Image Quant (Molecular Dynamics). Hard copies were obtained by exposing blots to Hyper Film (Amersham).

3. In situ hybridization

Animals were killed by $CO_2$ overdose and immediately perfused with PBS and then with 4% paraformaldehyde in 0.1 M phosphate buffer, pH 7.4. Eyes were enucleated and the cornea and lens were removed. The rest of the eye was post-fixed in 4% paraformaldehyde overnight and then in 30% sucrose in PBS for 4 hr. Eyes were embedded in Tissue-Tek O.C.T. compound (Miles Inc., Elkhart, Ind.), frozen in powdered dry ice, and stored at −80° C. Sections of 15–20 μm were cut through the entire retina, along the vertical meridian, on a Cryostat at −20° C. and thaw-mounted onto Super Frost Plus glass slides (Fisher Scientific, Pittsburgh, Pa.). Sections on the glass slides were air dried for 2 hr and fixed in 4% paraformaldehyde for 20 min before treatment with 10 μg/ml proteinase K for 10 min at 37° C. Sections then were washed and treated with 0.25% acetic anhydride and 0.1 M triethanolamine, pH 8.0, for 10 min, 0.1 M Tris/glycine buffer (pH 7.0) for 30 min, dehydrated in graded alcohols, and air dried. Then sections were hybridized with $^{35}S$ labeled antisense RNA probe for rat bFGF ($10^7$ cpm/ml) at 50° C. overnight. Some sections were hybridized with sense probe, which served as a control for non-specific labeling. The hybridization buffer contained 40% formamide, 4xSSC, 1 mg/ml yeast tRNA, 1 mg/ml denatured salmon sperm DNA, 10% dextran sulfate, 10 mM DTT, and 5xDenhardt's solution. After hybridization, sections were washed twice in 2xSSC for 10 min at room temperature, once in 50% formamide, 2xSSC at 52° C. for 10 min, and then were treated with RNase A (10 mg/ml) in 2xSSC for 20 min at 37°. Sections were washed once again in 50% formamide, 2xSSC for 10 min at 52° C. and then 2xSSC, 0.05% Triton X-100 for 1 hr at room temperature. Finally, sections were dehydrated in graded alcohols, and cleaned in xylene. Slides were coated with NTB-3 photoemulsion (Eastman Kodak, Rochester N.Y.), exposed at 4° C. for 10–20 d, and then developed.

4. Histology and constant light exposure

Animals were injected systemically with either xylazine or clonidine according to a 10 d injection protocol, starting 4 d before constant-light exposure and continuing throughout the constant light exposure. An additional 4 d injection protocol was used for xylazine injection, in which injection was given each day for 4 d immediately before constant light exposure, but no injection during the 7 d constant light exposure. For constant light exposure, animals were placed into constant fluorescent light at a illuminance of 115–130 ft-c for a period of 7 d. Then animals were killed by overdose of $CO_2$ followed immediately by vascular perfusion of mixed aldehydes and eyes were embedded in an Epon/Araldite mixture for sectioning at 1 mm thickness to provide sections of the entire retina along the vertical meridian of the eye (LaVail et al. *Exp. Eye. Res.* 21:167–192 (1975)).

B. Results and Discussion

In early studies, an unexpected transient increase in bFGF mRNA was observed in the retinas of sham-operated eyes (not shown). To determine whether the increase in bFGF mRNA was induced by ketamine or xylazine, animals were injected with either a ketamine-xylazine mixture ((ket+xyl), ketamine, 40 mg/kg, xylazine 6 mg/kg, i.m.), ketamine alone ((ket) 40 mg/kg, i.m.), xylazine alone ((xyl) 6 mg/kg, i.m.), or PBS (phosphate buffered saline, 0.5 ml, i.m.). Control animals were uninjected. bFGF mRNA was examined in the retina 12 hr after injection. Northern blot analysis, with radioactively labeled DNA probes complementary to mRNA encoding bFGF, detected a major bFGF transcript of 7.0 kb, alone with several smaller transcripts (FIG. 1A). A significant increase in bFGF mRNA was observed in animals injected with the ketamine-xylazine mixture or xylazine. Quantitative analysis of this transcript indicated that there was a 4.5-fold increase in retinas of ketamine-xylazine injected animals, and also a 4.5-fold increase in retinas of xylazine-treated animals. No significant change was observed in either ketamine or PBS treated animals. Thus, xylazine, an $\alpha_2$-adrenergic agonist, was responsible for the increase in bFGF mRNA observed in sham-operated eyes.

Figure 1B:
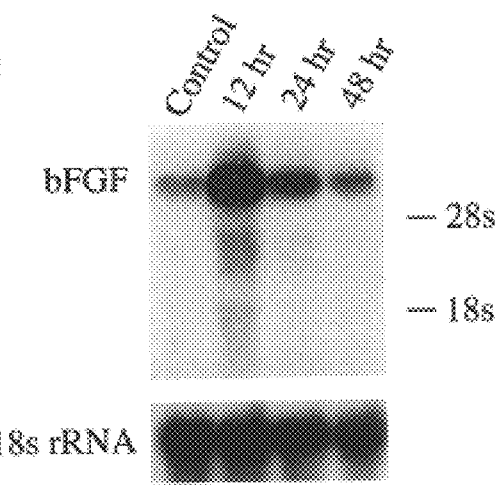

To characterize further the effect of xylazine on bFGF mRNA expression in the retina, animals were injected with xylazine (6 mg/kg, i.m.) and bFGF mRNA levels estimated in the retinas 12, 24, and 48 hr after the injection. As shown in FIG. 1B, the xylazine-induced bFGF expression was transient. Expression of bFGF mRNA increased 5.7-fold 12 hr after xylazine injection. By 24 hr, it had declined to about 2-fold, and had returned to the control level by 48 hr.

Figure 1C:
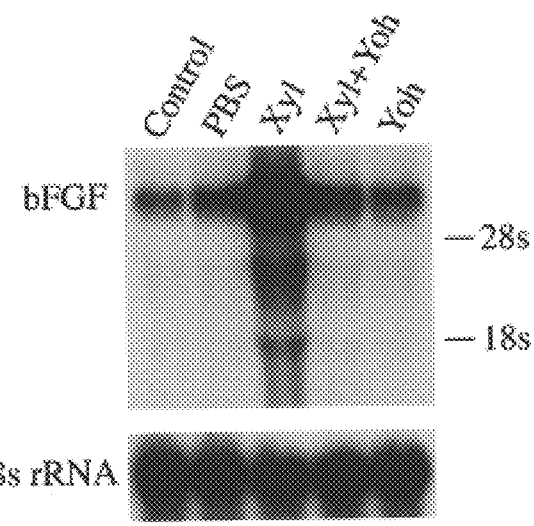

To confirm that the xylazine effect on bFGF mRNA expression was mediated via $\alpha_2$-adrenergic receptors, yohimbine, a specific $\alpha_2$-adrenergic antagonist, was used. Animals were injected with PBS (0.5 ml, i.m.), or xylazine (xyl) (6 mg/kg, i.m.), or yohimbine (5 mg/kg, i.p., 20 min before xylazine) plus xylazine (yoh+xyl), or yohimbine alone (yoh) (5 mg/kg, i.p.). When injected (5 mg/kg, i.p.) 20 min before xylazine, yohimbine completely blocked the effect of xylazine (FIG. 1C). The complete inhibition of the xylazine-induced bFGF expression provides additional evidence that the effect of xylazine was mediated via $\alpha_2$-adrenergic receptors. Furthermore, injection of hydralazine (5 mg/kg, i.m.), which reduces mean arterial blood pressure substantially (Burney et al. *Acta. Oncologica.* 34:367–371 (1995)), produced only a small increase (40%) in bFGF expression in the retina (not shown), indicating that reduction in blood pressure had only a small contribution to the increase in bFGF expression induced by xylazine.

Figure 2A:
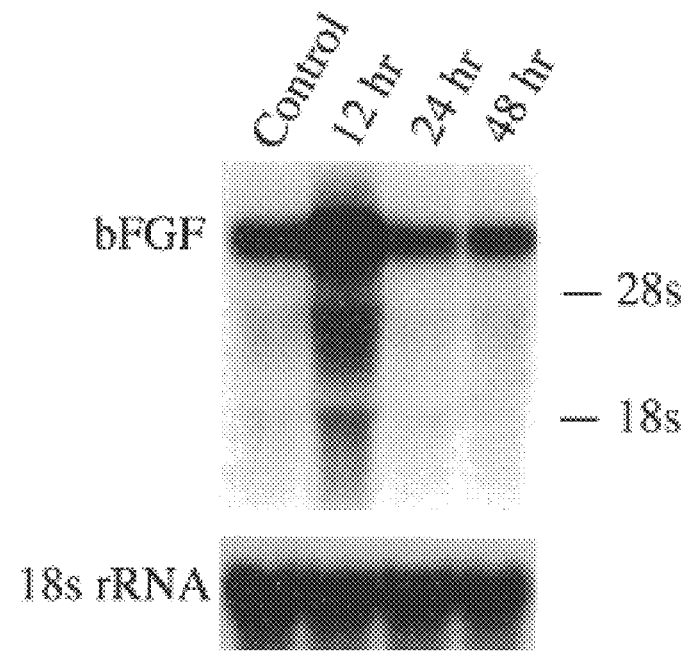
FIGS. 2(A–B) depicts (A) time course of clonidine induced bFGF expression and (B) inhibition of clonidine effect by yohimbine.
Figure 2B:
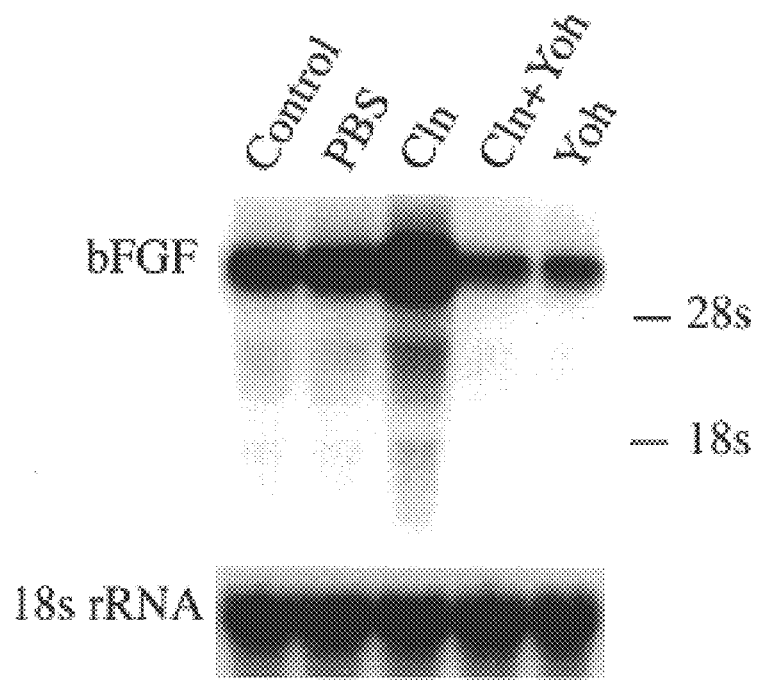

Clonidine, another $\alpha_2$-adrenergic agonist, was used to confirm further that the activation of $\alpha_2$-adrenergic receptors was responsible for the induction of bFGF expression. Animals were injected with clonidine (0.5 mg/kg, i.p.) and retinas were collected 12, 24, or 48 hr after injection. The temporal pattern of bFGF mRNA expression after a single injection of clonidine was very similar to that of xylazine. There was a transient increase (3.2-fold) in bFGF mRNA 12 hr after injection, which declined to baseline level by 24 hr after injection (FIG. 2A). In FIG. 2B, animals were injected with PBS (0.5 ml, i.m.), or clonidine (cln) (0.5 mg/kg, i.m.), or yohimbine (15 mg/kg, i.p., 20 min before clonidine) plus clonidine (yoh+cln), or yohimbine alone (yoh) (15 mg/kg, i.p.). Pretreatment with yohimbine (15 mg/kg, i.p.) 20 min before clonidine injection completely inhibited the clonidine effect on bFGF expression (FIG. 2B). In addition, at this dosage, yohimbine also inhibited the normal expression of bFGF in the retina by 40% (FIG. 2B).

To determine whether xylazine or clonidine induced bFGF expression in the brain as well, animals were injected with either xylazine ((xyl) 6 mg/kg, i.m.) or clonidine ((cln) 0.5 mg/kg, i.p.) and eight brain regions—septum (sep), striatum (stri), thalamus (th), hypothalamus (hy), hippocampus (hip), olfactory bulb (OB), cerebellum (Cb), and cerebral cortex (Cx)—were dissected 12 hr after injection.

Figure 3A:
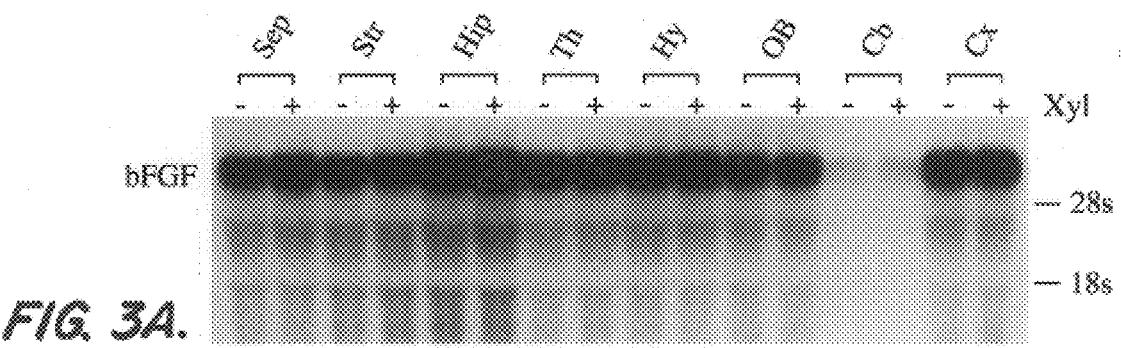
FIG. 3 depicts (A) expression of bFGF in the brain in animals (A) xylazine (xyl) or (B) clonidine (cln).
Figure 3B:
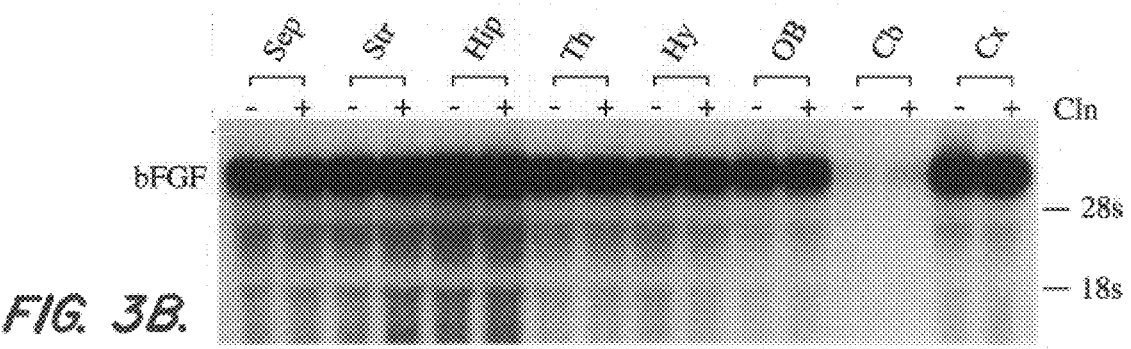

Northern blot analysis showed virtually no change in bFGF mRNA expression after either xylazine (FIG. 3A) or clonidine (FIG. 3B) injection in any of the brain regions. These findings indicated that both xylazine- and clonidine-dependent bFGF expression is selective for the retina.

To localize the xylazine-induced bFGF mRNA expression, we performed in situ hybridization with radioactively labeled RNA probes complementary to mRNA encoding bFGF. Animals were injected with xylazine (6 mg/kg) and eyes were collected 12 hr after injection. In the normal retina, bFGF mRNA was expressed at a low level in the retinal pigment epithelium (RPE), the inner segments of photoreceptors, the inner nuclear layer, and the ganglion cell layer (data not shown). After xylazine injection, the increased bFGF mRNA was found almost exclusively in the inner segments of photoreceptors, whereas little change in expression was observed in the other regions of the retina (data not shown). Retinas hybridized with sense probe showed non-specific hybridization that did not form any specific pattern (data not shown).

To determine whether induction of bFGF expression by $\alpha_2$-adrenergic agonists in photoreceptors could protect them from cell death in a retinal degeneration, a constant light induced photoreceptor degeneration in albino rats model was used. Because the induction of bFGF expression by xylazine or clonidine injection was transient, a multiple injection protocol was used to produce a sustained up-regulation of bFGF expression. In this protocol (10 d injection), systemic injection of either xylazine or clonidine was given each day starting 4 d before constant light exposure and continuing throughout the constant light exposure. An additional protocol (4 d injection) for xylazine injection was used to determine whether stimulation of bFGF expression in the retina before constant light exposure would ameliorate light damage. In the 4 d injection protocol, systemic injection of xylazine was given each day for 4 d immediately prior to constant light exposure, but no injections were given during the 7 d constant light exposure.

Severe photoreceptor degeneration was observed in uninjected animals after 7 d of constant light exposure. The outer nuclear layer, where photoreceptor nuclei reside, was reduced from 10–11 rows of nuclei in normal animals to 3–4 rows (data not shown). There was almost a complete absence of photoreceptor inner segments, and outer segments that remained formed large rounded or oblong profiles (data not shown). In injected animals, however, the photoreceptor degeneration was much less severe. There were, on average, 6–8 rows of photoreceptor nuclei in the outer nuclear layer (ONL). The inner segments, shorter than normal, were present. The outer segments were better preserved, although many also showed the rounded and oblong profiles (data not shown).

Figure 4:
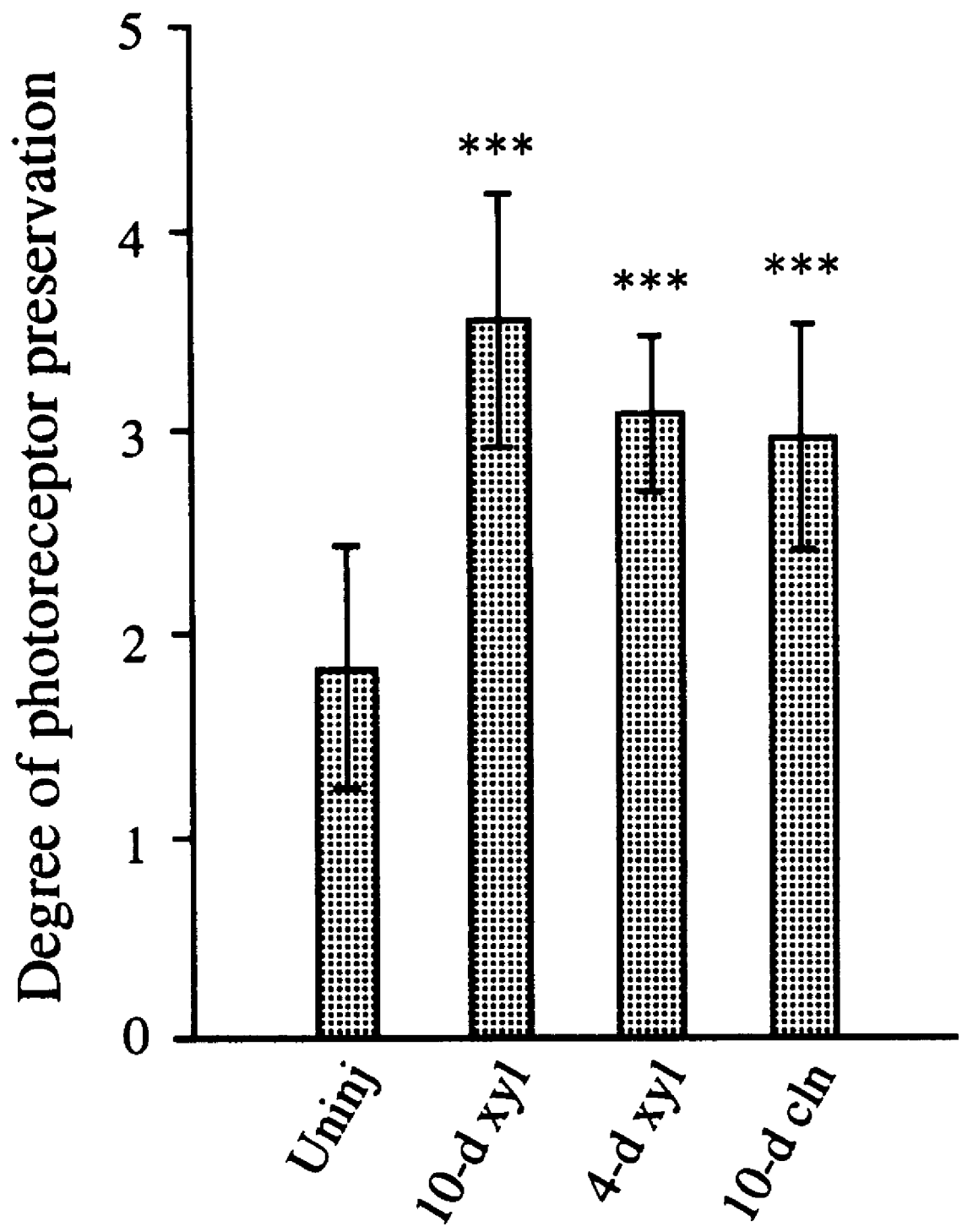
FIG. 4 depicts the degree of photoreceptor preservation in retinas of rats injected with xylazine or clonidine and exposed to constant light.

To assess the degree of photoreceptor preservation after constant light exposure, a scoring system was used that took into account the well known nonuniform distribution of light damage across the retina and, in each retinal region, the number of surviving photoreceptor nuclei as well as the condition of the inner and outer segments. A five point scale was used, with the score for normal retina being five and the score being one for retina with the most severe loss of photoreceptors. Each tissue section was assessed in a double-blind manner by four scientists equally familiar with the scoring criteria, with the final score being given by unanimous decision. In uninjected animals, the degree of photoreceptor preservation after 7 d of constant light exposure was $1.83 \pm 0.60$ (mean$\pm$SD, n=23), whereas in all three groups of animals receiving xylazine or clonidine injection, the degrees of photoreceptor preservation was significantly higher. The score for animals receiving the 10 d injection of xylazine (xyl) was $3.54 \pm 0.63$ (n=34), $3.08 \pm 0.39$ (n=18) for 4 d injection of xylazine, and $2.97 \pm 0.55$ (n=15) for the 10 d injection of clonidine (cln) (FIG. 4).

Thus, the systemic administration of $\alpha_2$-adrenergic agonists increased bFGF mRNA mainly in the photoreceptors of rat retina, but not in the brain, via activation of $\alpha_2$-adrenergic receptors. Without being limited to any one theory, a likely scenario is that the increase in bFGF mRNA expression results from direct stimulation of $\alpha_2$-adrenergic receptors in photoreceptors by the agonists. In cultured chromaffin cells from bovine adrenal medulla, it has been shown that direct stimulation of nicotinic acetylcholine receptors or angiotensin II receptors increased bFGF protein expression via cAMP or protein kinase C pathways, respectively (Stachowiak et al. *J. Cell. Biol.* 127:203–223 (1994)). Because $\alpha_2$-adrenergic receptors are believed to be coupled negatively to adenylate cyclase (Jakobs *Mo. Cell. Endo.* 16:147–156 (1979); Bylund *FASEB J* 6:832–839 (1992)), and it has been shown that direct stimulation of $\alpha_2$-adrenergic receptors resulted in inhibition of cAMP production in the rabbit retina (Osborne *Brain. Res.* 553:84–88 (1991)), the results of the instant invention support a new regulatory mechanism for bFGF expression.

In comparable experiments to those described herein, $\beta$-adrenergic agonists also caused upregulation of bFGF in the retina, following the same time course as the $\alpha$-adrenergic agonists. Moreover, $\beta$-adrenergic agonists also protected photoreceptors from constant light-induced degeneration.

All references cited herein are specifically incorporated by reference in their entirety for all purposes.

What is claimed is:

1. A method for treating a retinal disease or condition, which disease or condition causes injury or death of photoreceptors, said method comprising administering to a patient suffering from said retinal disease or condition a therapeutically effective dose of an alpha-adrenergic agonist.

2. The method of claim 1, wherein the agonist is administered systemically.

3. The method of claim 1, wherein the agonist is administered to the eye.

4. The method of claim 1 wherein bFGF expression is stimulated in retinal cells in the patient.

5. The method of claim 4, wherein the retinal cells are photoreceptors.

6. The method of claim 5, wherein the photoreceptors are injured.

7. The method of claim 5, wherein the photoreceptors are dying.

8. A method for treating a retinal disease or condition, which disease or condition causes injury or death of photoreceptors, said method comprising administering to a patient suffering from said retinal disease or condition a therapeutically effective dose of a beta-adrenergic agonist.

9. The method of claim 8, wherein the agonist is administered systemically.

10. The method of claim 8, wherein the agonist is administered to the eye.

11. The method of claim 8, wherein bFGF expression is stimulated in retinal cells in the patient.

12. The method of claim 2, wherein the retinal cells are photoreceptors.

13. The method of claim 12, wherein the photoreceptors are injured.

14. The method of claim 12, wherein the photoreceptors are dying.

15. The method of claim 9, wherein the alpha-adrenergic agonist is selected from the group consisting of norepinephrine, clonidine, guanfacine, azepexole, B-HT 920, UK 14,304, epinephrine, dipivefrin, apraclonidine, brimonidine, agmatine, p-aminoclonidine, guanabenz, p-iodoclonidine, oxymetazoline, and xylazine.

16. The method of claim 1, wherein the beta-adrenergic agonist is selected from the group consisting of norepinephrine, epinephrine, salbutamol, dobutamine, icoproterenol nylidrin and clenbuterol.

* * * * *

UNITED STATES PATENT AND TRADEMARK OFFICE
CERTIFICATE OF CORRECTION

| | |
|---|---|
| PATENT NO. | : 6,066,675 |
| APPLICATION NO. | : 08/925544 |
| DATED | : May 23, 2000 |
| INVENTOR(S) | : Wen et al. |

Page 1 of 1

It is certified that error appears in the above-identified patent and that said Letters Patent is hereby corrected as shown below:

<u>Column 11, line 3</u>:

Delete "The method of claim 9," and replace it with:

-- The method of claim 1, --

<u>Column 12, line 1</u>:

Delete "The method of claim 1," and replace it with:

-- The method of claim 8, --

Signed and Sealed this

Twenty-fifth Day of March, 2008

JON W. DUDAS
*Director of the United States Patent and Trademark Office*